United States Patent
Gu et al.

(10) Patent No.: US 7,547,713 B2
(45) Date of Patent: Jun. 16, 2009

(54) O-PYRIDINEQUINONE DERIVATIVES, THE COMPOSITION CONTAINING THE DERIVATIVES, THE PROCESS FOR PREPARATION OF THE DERIVATIVES AND THE USE OF THE DERIVATIVES

(76) Inventors: Lianquan Gu, Room 604-602, Po Yuan, Zhongshan University, 135 Xin Gang XI Road, Guangzhou, Guangdong Province (CN) 510275; Jun Wang, 23B Block 1, New Town Plaza, Phase 3, Shatin, N.T., Hong Kong (CN); Guiwu Xiao, Room 27G, YI Hui Jiu, Hua Jing Xin Cheng, Tian He, Guangzhou, Guangdong Province (CN) 510630

( * ) Notice: Subject to any disclaimer, the term of this patent is extended or adjusted under 35 U.S.C. 154(b) by 528 days.

(21) Appl. No.: 10/525,352

(22) PCT Filed: Aug. 22, 2003

(86) PCT No.: PCT/CN03/00711

§ 371 (c)(1),
(2), (4) Date: Sep. 2, 2005

(87) PCT Pub. No.: WO2004/018427

PCT Pub. Date: Mar. 4, 2004

(65) Prior Publication Data

US 2006/0111405 A1    May 25, 2006

(30) Foreign Application Priority Data

Aug. 23, 2002  (CN) ................ 02 1 30161

(51) Int. Cl.
*C07D 213/69* (2006.01)
*A61K 31/4412* (2006.01)
(52) U.S. Cl. ........................ 514/348; 546/296
(58) Field of Classification Search ............... None
See application file for complete search history.

(56) References Cited

FOREIGN PATENT DOCUMENTS

| CN | 1431242 A | 7/2003 |
|---|---|---|
| WO | WO 00/37426 * | 6/2000 |

\* cited by examiner

*Primary Examiner*—Zinna N Davis
(74) *Attorney, Agent, or Firm*—Frommer Lawrence & Haug LLP; Ronald R. Santucci

(57) ABSTRACT

The present invention relates to the o-pyridinequinone disubstituted derivatives, the composition containing the derivatives, the process for preparation of the derivatives and the use of the derivatives. The o-pyridinequinone disubstituted derivatives of the present invention have action of selectivity inhibiting COX-2 and they can be made into pharmaceuticals. The o-pyridinequinone disubstituted derivatives of the present invention have no acute toxicities and are a safe pharmaceutical.

31 Claims, 1 Drawing Sheet

O-PYRIDINEQUINONE DERIVATIVES, THE COMPOSITION CONTAINING THE DERIVATIVES, THE PROCESS FOR PREPARATION OF THE DERIVATIVES AND THE USE OF THE DERIVATIVES

This application is a 371 of PCT/CN2003/000711 filed on Aug. 22, 2003, published on Mar. 4, 2004 under publication number WO 2004/018427 A1 which claims priority benefits from Chinese Patent Application Number 02130161.1 filed Aug. 23, 2002.

FIELD OF THE INVENTION

The present invention relates to a compound having anti-inflammatory activity and which may be used as an agent selectively inhibiting cyclooxygenase-2 (COX-2) in inflammatory cells, to a method of preparing the compound, to a composition comprising the compound and to a use thereof. Specifically, the present invention relates to a compound derivative having o-pyridinequinone structure, a method for preparation thereof, a composition comprising the derivative and a use thereof.

BACKGROUND OF THE INVENTION

Aspirin, marketed by Bayer AG (Germany) in last-century, is a famous anti-inflammatory, antipyretic, and analgesic agent. Although the commonly used anti-inflammatory agents such as aspirin have favorable anti-inflammatory, antipyretic, and analgesic effects, they exhibit apparent toxicity on gastrointestinal tracts and kidneys. The toxic and side effects of aspirin are due to that aspirin is not a specific COX-2 inhibiting agent.

Studies have proven that, endosomatic cyclooxygenases have two kinds of subtypes: COX-1 and COX-2. COX-1 is present in normal tissue cells and plays an important role in protecting mucous cells of gastrointestinal tracts and maintaining the normal functions of blood platelets and kidneys. COX-2 is mainly present in inflammation tissues. COX-2 can promote the production of various prostaglandins by inflammatory cells, induce inflammatory response, and thus cause pain and pyrexia and the like symptoms. Recent studies indicate that the activity of COX-2 in tumour tissues is higher than that in normal tissues.

The results of amino acid sequencing and X-ray diffraction on structures of cyclooxygenases indicate that COX-1 and COX-2 have approximately 60% identity in their amino acid sequences and the main catalytic groups in their catalysis active centers are substantially similar, with only small differences, such as COX-1 having isoleucine-523, while COX-2 has valine-523. In addition, the amino acid residues at the entrance of the active center of COX-1 are also different from those of COX-2.

Aspirin can not distinguish the structural differences between COX-1 and COX-2. Aspirin can acylate serine-530 of both COX-1 and COX-2. As a result, the actions of both COX-1 and COX-2 are inhibited. Therefore, the anti-inflammatory agents, for example, the nonspecific COX inhibiting agents such as Aspirin, inhibit not only the production of prostaglandins which participate in inflammatory responses, but also the syntheses of prostaglandins which bring normal physiological effects, and result in toxic and side effects.

DISCLOSURE OF THE INVENTION

An object of the present invention is to provide a compound represented by formula I, which is a disubstituted derivative having o-pyridinequinone structure:

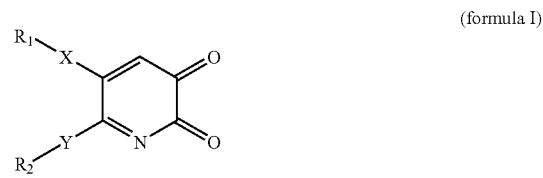

(formula I)

wherein:

$R_1$ and $R_2$ may be the same or different, each independently represents substituted or unsubstituted phenyl, pyridinyl or pyrimidinyl, X and Y may be the same or different, each independently represents an N or S atom, provided that when X or Y represents S, then the $R_1$ or $R_2$ attached to the S atom is substituted or unsubstituted phenyl.

Formula I, which shows a o-pyridinequinone disubstituted derivative, specifically refers to a 5,6-disubstituted-2,3-pyridindione compound.

When $R_1$ or $R_2$ represents substituted phenyl, pyridinyl or pyrimidinyl, the phenyl, pyridinyl or pyrimidinyl preferably has one to three substituents independently selected from the group consisting of $C_1$-$C_6$ linear or branched alkyl, $C_1$-$C_6$ linear or branched alkoxyl, halogen, amino, di($C_1$-$C_3$ alkyl) amino, carbamyl, sulfamoyl, sulfo, cyano, nitro, carboxyl, hydroxy, hydroxyl($C_1$-$C_3$)alkyl, ($C_1$-$C_3$ allyl)acyl and ($C_1$-$C_3$ alkyl)thio.

The term "$C_1$-$C_6$ linear or branched alkyl" is, for example, methyl, ethyl, n-propyl, isopropyl, n-butyl, isobutyl, sec-butyl, tertiary butyl, pentyl, isopentyl, neopentyl, n-hexyl and the like. Among these, methyl, ethyl, propyl and butyl are preferable; methyl and ethyl are more preferable.

The term "$C_1$-$C_6$ linear or branched alkoxyl" is, for example, methoxy, ethoxy, n-propoxy, isopropoxy, n-butoxy, isobutoxy, sec-butoxy, tert-butoxy, pentyloxy, isopentyloxy, neopentyloxy, n-hexyloxy and the like. Among these, methoxy, ethoxy, n-propoxy, isopropoxy, n-butoxy, isobutoxy, sec-butoxy, and tert-butoxy are preferable; methoxy and ethoxy are more preferable.

The term "halogen" is fluoro, chloro, bromo or iodo. Among these, fluoro, chloro, and bromo are preferable.

In a preferable embodiment, $R_1$, together with X to which $R_1$ is attached, form p-tolylamino, o-tolylamino, m-tolylamino, p-ethylphenylamino, o-ethylphenylamino, m-ethylphenylamino, p-chlorophenylamino, o-chlorophenylamino m-chlorophenylamino, p-fluorophenylamino, o-fluorophenylamino, m-fluorophenylamino, p-bromophenylamino, o-bromophenylamino, m-bromophenylamino, p-iodophenylamino, o-iodophenylamino, m-iodophenylamino, p-nitrophenylamino, o-nitrophenylamino, m-nitrophenylamino, p-carboxylphenylamino, o-carboxylphenylamino, m-carboxylphenylamino, p-carbamoylphenylamino, o-carbamoylphenylamino, m-carbamoylphenylamino, p-methoxyphenylamino, o-methoxyphenyl amino, m-methoxyphenylamino, p-ethoxyphenylamino, o-ethoxyphenylamino, m-ethoxyphenylamino, p-sulfophenylamino, o-sulfophenylamino, m-sulfophenylamino, p-sulfamoylphenylamino, o-sulfamoylphenylamino, m-sulfamoylphenylamino, p-cyanoylphenylamino, o-cyanoylphenylamino, m-cyanoylphenylamino, p-hydroxymethylphenylamino, o-hydroxymethylphenylamino, m-hydroxymethylphenylamino, p-acetylphenylamino, o-acetylphenylamino, m-acetylphenylamino, p-acetaminophenylamino, o-acetaminophenylamino, m-acetaminophenylamino, p-N,N-dimethylaminophenylamino, o-N,N-dimethylaminophenylamino, m-N,N-dimethylaminophenylamino, 2-carboxyl-4-bromophenylamino, 2-carboxyl-6-chlorophenylamino, 2-carboxyl-5-chlorophenylamino, 2-carboxyl-4-chlorophenylamino, 2-carboxyl-3-chlorophenylamino, 3-carboxyl-2-chlorophenylamino, 3-carboxyl-6-chlorophenylamino, 3-carboxyl-4-chlorophenylamino, 4-carboxyl-3-chlorophenyl amino, 2-cyano-5-chlorophenylamino, 2-hydroxymethyl-4-chlorophenylamino, 4-carboxyl-5-methoxy-2-chlorophenylamino, 2-sulfo-4-methyl-5-chlorophenylamino, 2-methyl-4-nitro-5-chlorophenylamino, 2-carboxyl-4,6-dichlorophenylamino, 2-carboxyl-4,6-diiodophenylamino, 4-carboxyl-2,6-diiodophenylamino, 2-carboxyl-4,6-dimethoxyphenylamino, 2-cyano-4,6-dimethoxyphenylamino, 4-carbamoyl-2,6-dinitrophenylamino, 2-carboxyl-5-fluorophenylamino, 2-carboxyl-4-fluorophenylamino, 2-carboxyl-3-fluorophenylamino, 2-cyano-3-fluorophenylamino, 2-carboxyl-4-iodophenylamino, 2-carboxyl-6-methoxyphenylamino, 3-carboxyl-6-methoxyphenylamino, 4-carboxyl-6-methoxyphenylamino, 2-carboxyl-4-methylphenylamino, 2-carboxyl-3-methylphenylamino, 3-carboxyl-2-methylphenylamino, 4-carboxyl-2-methylphenylamino, 5-carboxyl-2-methylphenylamino, 2-cyano-5-methylphenylamino, 2-hydroxymethyl-6-methylphenylamino, 2-hydroxymethyl-4-methylphenylamino, 2-methyl-3-hydroxymethylphenylamino, 2-methyl-5-hydroxymethylphenylamino, 2-cyano-4-nitrophenylamino, 4-cyano-2-nitrophenylamino, 2-methyl-4-nitrophenylamino, 2-hydroxy-3-carboxylphenylamino, 3-hydroxy-4-carboxylphenylamino, 3-carboxyl-4-hydroxyphenylamino, 4-sulfo-2-methylphenylamino, 3-sulfo-4-methylphenylamino, 2-sulfo-4-methylphenylamino, phenylthio, p-methylphenylthio, o-methylphenylthio, m-methylphenylthio, 2-carboxylphenylthio, pyridin-2-amino, pyridin-3-amino, pyridin-4-amino, 5-bromopyridin-2-amino, 5-bromo-3-nitropyridin-2-amino, 4-methyl-3-nitropyridin-2-amino, 4-methyl-5-nitropyridin-2-amino, 3-nitropyridin-2-amino, 5-nitropyridin-2-amino, 3-methylpyridin-2-amino, 4-methylpyridin-2-amino, 5-methylpyridin-2-amino, 6-methylpyridin-2-amino, 4,6-dimethylpyridin-2-amino, 2-methoxypyridin-5-amino, 5-chloropyridin-2-amino, 2-chloropyridin-3-amino, 2-chloropyridin-5-amino, 3,5-dibromopyridin-2-amino, 3,5-dichloropyridin-2-amino, 4-methyl-3-nitropyridin-2-amino, 4-methyl-5-nitropyridin-2-amino, nicotinamid-6-amino, nicotinamid-2-amino, pyrimidin-2-amino, pyrimidin-4-amino, 5-bromopyrimidin-2-amino, 2,6-dihydroxypyrimidin-4-amino, 4,6-dimethoxypyrimidin-3-amino, 4,6-dimethoxypyrimidin-2-amino, 4-hydroxy-6-methylpyrimidin-2-amino, 3-hydroxypyrimidin-2-amino, 4-methoxy-5-methylpyrimidin-2-amino, 2-methoxypyrimidin-5-amino, 4-chloro-6-methylpyrimidin-2-amino, 6-chloro-2-methylthiopyrimidin-4-amino, 4,6-dichloropyrimidin-2-amino, 4,6-dichloropyrimidin-5-amino, 4-methylpyrimidin-2-amino, 3-nitropyrimidin-2-amino or 5-nitropyrimidin-2-amino.

In a preferable embodiment, $R_2$, together with Y to which it is attached, form p-tolylamino, o-tolylamino, m-tolylamino, p-ethylphenylamino, o-ethylphenylamino, m-ethylphenylamino, p-chlorophenylamino, o-chlorophenylamino, m-chlorophenylamino, p-fluorophenylamino, o-fluorophenylamino, m-fluorophenylamino, p-bromophenylamino, o-bromophenylamino, m-bromophenylamino, p-iodophenylamino, o-iodophenylamino, m-iodophenylamino, p-nitrophenylamino, o-nitrophenylamino, m-nitrophenylamino, p-carboxylphenylamino, o-carboxylphenylamino, m-carboxylphenylamino, p-carbamoylphenylamino, o-carbamoylphenylamino, m-carbamoylphenylamino, p-methoxyphenylamino, o-methoxyphenylamino, m-methoxyphenylamino, p-ethoxyphenylamino, o-ethoxyphenylamino, m-ethoxyphenylamino, p-sulfophenylamino, o-sulfophenylamino, m-sulfophenylamino, p-sulfamoylphenylamino, o-sulfamoylphenylamino, m-sulfamoylphenylamino, p-cyanoylphenylamino, o-cyanoylphenylamino, m-cyanoylphenylamino, p-hydroxymethylphenylamino, o-hydroxymethylphenylamino, m-hydroxymethylphenylamino, p-acetylphenylamino, o-acetylphenylamino, m-acetylphenylamino, p-acetaminophenylamino, o-acetaminophenylamino, m-acetaminophenylamino, p-N,N-dimethylaminophenylamino, o-N,N-dimethylaminophenylamino, m-N,N-dimethylaminophenylamino, 2-carboxyl-4-bromophenylamino, 2-carboxyl-6-chlorophenylamino, 2-carboxyl-5-chlorophenylamino, 2-carboxyl-4-chlorophenylamino, 2-carboxyl-3-chlorophenylamino, 3-carboxyl-2-chlorophenylamino, 3-carboxyl-6-chlorophenylamino, 3-carboxyl-4-chlorophenylamino, 4-carboxyl-3-chlorophenylamino, 2-cyano-5-chlorophenylamino, 2-hydroxymethyl-4-chlorophenylamino, 4-carboxyl-5-methoxy-2-chlorophenylamino, 2-sulfo-4-methyl-5-chlorophenylamino, 2-methyl-4-nitro-5-chlorophenylamino, 2-carboxyl-4,6-dichlorophenylamino, 2-carboxyl-4,6-diiodophenylamino, 4-carboxyl-2,6-diiodophenylamino, 2-carboxyl-4,6-dimethoxyphenylamino, 2-cyano-4,6-dimethoxyphenylamino, 4-carbamoyl-2,6-dinitrophenylamino, 2-carboxyl-5-fluorophenylamino, 2-carboxyl-4-fluorophenylamino, 2-carboxyl-3-fluorophenylamino, 2-cyano-3-fluorophenylamino, 2-carboxyl-4-iodophenylamino, 2-carboxyl-6-methoxyphenylamino, 3-carboxyl-6-methoxyphenylamino, 4-carboxyl-6-methoxyphenylamino, 2-carboxyl-4-methylphenylamino, 2-carboxyl-3-methylphenylamino, 3-carboxyl-2-methylphenylamino, 4-carboxyl-2-methylphenylamino, 5-carboxyl-2-methylphenylamino, 2-cyano-5-methylphenylamino, 2-hydroxymethyl-6-methylphenylamino, 2-hydroxymethyl-4-methylphenylamino, 2-methyl-3-hydroxymethylphenylamino, 2-methyl-5-hydroxymethylphenylamino, 2-cyano-4-nitrophenylamino, 4-cyano-2-nitrophenylamino, 2-methyl-4-nitrophenylamino, 2-hydroxy-3-carboxylphenylamino, 3-hydroxy-4-carboxylphenylamino, 3-carboxyl-4-hydroxyphenylamino, 4-sulfo-2-methylphenylamino, 3-sulfo-4-methylphenylamino, 2-sulfo-4-methylphenylamino, phenylthio, p-methylphenylthio, o-methylphenylthio, m-methylphenylthio, 2-carboxylphenylthio, pyridin-2-amino, pyridin-3-amino, pyridin-4-amino, 5-bromopyridin-2-amino, 5-bromo-3-nitropyridin-2-amino, 4-methyl-3-nitropyridin-2-amino, 4-methyl-5-nitropyridin-2-amino, 3-nitropyridin-2-amino, 5-nitropyridin-2-amino, 3-methylpyridin-2-amino, 4-methylpyridin-2-amino, 5-methylpyridin-2-amino, 6-methylpyridin-2-amino, 4,6-dimethylpyridin-2-amino, 2-methoxypyridin-5-amino, 5-chloropyridin-2-amino, 2-chloropyridin-3-amino, 2-chloropyridin-5-amino, 3,5-dibromopyridin-2-amino, 3,5-dichloropyridin-2-amino, 4-methyl-3-nitropyridin-2-amino, 4-methyl-5-nitropyridin-2-amino, nicotinamid-6-amino, nicotinamid-2-amino, pyrimidin-2- amino, pyrimidin-4-amino, 5-bromopyrimidin-2-amino, 2,6-dihydroxypyrimidin-4-amino, 4,6-dimethoxypyrimidin-3-amino, 4,6-dimethoxypyrimidin-2-amino, 4-hydroxy-6-methylpyrimidin-2-amino, 3-hydroxypyrimidin-2-amino, 4-methoxy-5-methylpyrimidin-2-amino, 2-methoxypyrimidin-5-amino, 4-chloro-6-methylpyrimidin-2-amino, 6-chloro-2-methylthiopyrimidin-4-amino, 4,6-dichloropyrimidin-2-amino, 4,6-dichloropyrimidin-5-amino, 4-methylpyrimidin-2-amino, 3-nitropyrimidin-2-amino or 5-nitropyrimidin-2-amino.

Specifically, the most preferable compounds of the present invention are selected from the following:
5,6-dichloro-2,3-pyridindione,
5,6-diphenylamino-2,3-pyridindione,
5-phenylamino-6-(o-chlorophenylamino)-2,3-pyridindione,
6-phenylamino-5-(o-chlorophenylamino)-2,3-pyridindione,
5,6-di(o-chlorophenylamino)-2,3-pyridindione,
5-p-methoxyphenylamino-6-(p-sulfoaminophenylamino)-2,3-pyridindione,
6-p-methoxyphenylamino-5-(p-sulfoaminophenylamino)-2,3-pyridindione,
5,6-di(p-methoxyphenylamino)-2,3-pyridindione,
5,6-di(p-sulfonylphenylamino)-2,3-pyridindione,
5,6-di(p-chlorophenylamino)-2,3-pyridindione,
5,6-di(chlorophenylamino)-2,3-pyridindione,
5,6-di(o-tolylamino)-2,3-pyridindione,
5,6-di(p-tolylamino)-2,3-pyridindione,
5-p-acetylphenylamino-6-phenylamino-2,3-pyridindione,
5,6-di(m-formylphenylamino)-2,3-pyridindione,
5,6-di(m-carboxylphenylamino)-2,3-pyridindione,
5,6-di(m-acetylphenylamino)-2,3-pyridindione,
5,6-di(p-carboxylphenylamino)-2,3-pyridindione.

The present invention further relates to a method of preparing the compound represented by formula I above, comprising the steps of:

reacting the compound represented by formula II

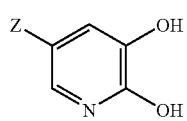

(formula II)

wherein Z is H or halogen,
with one or two aromatic amines represented by formula III
R$_4$NH$_2$ (formula III)
   wherein R$_4$ represents substituted or unsubstituted phenyl, pyridinyl or pyrimidinyl, or,
with one or two thiophenols represented by formula IV R$_5$SH  (formula IV)

wherein R$_5$ represents substituted or unsubstituted phenyl, in the presence of an oxidant at a temperature of 10-80° C. for 0.2-20 hr.

When Z, in formula II is halogen, it is preferably chloro or bromo.

When R$_4$ in formula III represents substituted phenyl, substituted pyridinyl or substituted pyrimidinyl, the phenyl, pyridinyl or pyrimidinyl has one to three substituents independently selected from the group consisting of C$_1$-C$_6$ linear or branched alkyl, C$_1$-C$_6$ linear or branched alkoxy, halogen, amino, di(C$_1$-C$_3$ alkyl)amino, aminoformyl, sulfamoyl, sulfo, cyano, nitro, carboxyl, hydroxy, hydroxy(C$_1$-C$_3$)alkyl, (C$_1$-C$_3$ alkyl)acyl and (C$_1$-C$_3$ alkyl)thio.

When R$_5$ in formula IV represents substituted phenyl, this phenyl has one or two substituents selected from the group consisting of methyl, ethyl, propyl and carboxyl.

There is no limitation on the oxidants used in the method of the present invention. The oxidant may be chemical oxidants, such as, at least one member selected from the group consisting of alkali salts of bromic acid, alkali salts of iodic acid, alkali salts of persulfuric acid, and alkali salts of chloric acid. Among these, the alkali metal is preferably sodium or potassium. The oxidants may also be oxidase enzymes; such as, polyphenoloxidases. The polyphenoloxidases useful in the present invention may be those obtained by separation from mushroom, potato, banana, eggplant and the like, as well as microorganisms. The polyphenoloxidases can also be a product obtained by a recombinant DNA technique. These enzymes may be used in the form of a crude extract or purified pure enzyme. Of course, immobilized enzymes may also be used.

In the method of the present invention, the reaction temperature is generally in the range of 10° C. to 80° C. When chemicals are used as the oxidants in the method of present invention, the reaction temperature is preferably in the range of 20° C. to 80° C., more preferably in the range of 40° C. to 60° C. When oxidases such as the polyphenoloxidases are used as the oxidants in the method of present invention, the reaction temperature is preferably in the range of 10° C. to 60° C., more preferably in the range of 25° C. to 45° C., most preferably in the range of 30° C. to 40° C.

In the method of the present invention, there is no particular limitation on the mode of adding the oxidants to reaction system. When the chemical oxidants are used, the oxidants, which have been dissolved in an aqueous solvent, may be added to reaction system at one time or added in portions. Moreover, the aqueous solvent may be mixed with one or more water miscible organic solvents in advance, then the chemical oxidants and the reactant represented by formula II or formula III are dissolved into the resulting mixture of solvents. The aqueous solvent herein comprises water and water solution, such as a phosphate buffer or Tris-HCl buffer, or water-organic solvent solution. However, to obtain a complete reaction, the solvent of the chemical oxidant is generally added to the reaction system in two to four portions. When the polyphenoloxidase is used as the oxidant, the reactant represented by formula II and the compound represented by formula IV or formula V as well as the polyphenoloxidase may be added into the phosphate buffer or Tris-HCl buffer having a particular pH value, or into the water-organic solvent solution, or into an aqueous or water-organic solution containing a surfactant, at a temperature of 10° C. to 60° C.

Those skilled in the art should understand that the reaction time will differ depending on the reaction temperature, the nature of reactant, and the kind and concentration of the oxidant used in the method of the present invention. However, the reaction is normally completed in 0.2 hr to 20 hrs. When the chemical oxidant is used, the reaction time is 0.2 hr to 10 hrs, and under the preferable conditions, the reaction is completed in 5 hrs. When the polyphenoloxidase is used as the oxidant, the reaction time is 0.2 hrs to 20 hrs, and under the preferable conditions, the reaction is completed in 8 hrs.

In the context of the present specification, there is no particular limitation on the organic solvent used in the method of the present invention, as long as it is miscible with water. Thus, the organic solvent useful herein includes, but is not limited to, methanol, ethanol, dimethyl sulfoxide, acetone, dioxane, tetrahydrofuran, dimethyl formamide, acetonitrile or the mixture thereof.

The activities of the compound of the present invention for inhibiting COX-1 and COX-2 were measured and investigated. The specific steps are described in the following experimental examples 1 and 2. The present inventors found that the o-pyridinequinone disubstituted derivatives or the pharmaceutical composition comprising the same have a considerably high inhibiting activity on COX-2 and a low inhibiting activity on COX-1, showing that the compound of the present invention has au excellent selectivity in inhibiting COX-2. Thus, the compound of the present invention is anticipated to be developed into a novel anti-inflammatory agent with high activity, low toxic and low side effects.

A fiber aspect of the present invention relates to a pharmaceutical composition containing the compound of formula I as an active component and a pharmaceutical acceptable carrier:

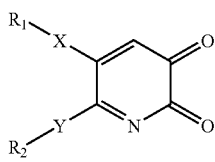

(formula I)

wherein:

$R_1$ and $R_2$ may be the same or different, each independently represents substituted or unsubstituted phenyl, pyridinyl or pyrimidinyl, X and Y may be the same or different, each independently represents an N or S atom, provided that when X or Y represents S, then the $R_1$ or $R_2$ attached to the S atom is substituted or unsubstituted phenyl.

When $R_1$ or $R_2$ represents substituted phenyl, substituted pyridinyl or substituted pyrimidinyl, the phenyl, pyridinyl, pyrimidinyl has preferably one to three substituents independently selected from the group consisting of $C_1$-$C_6$ linear or branched alkyl, $C_1$-$C_6$ linear or branched alkoxyl, halogen, amino, di($C_1$-$C_3$ alkyl)amino carbamyl, sulfamoyl, sulfo, cyano, nitro, carboxyl, hydroxy, hydroxy($C_1$-$C_3$)alkyl, ($C_1$-$C_3$ alkyl)acyl and ($C_1$-$C_3$ alkyl)thio.

Preferably, $R_1$—X— and $R_2$—Y— each is independently selected from the group consisting of p-tolylamino, o-tolylamino, m-tolylamino, p-ethylphenylamino, o-ethylphenylamino, m-ethylphenylamino, p-chlorophenylamino, o-chlorophenylamino, m-chlorophenylamino, p-fluorophenylamino; o-fluorophenylamino, m-fluorophenylamino, p-bromophenylamino, o-bromophenylamino, m-bromophenylamino, p-iodophenylamino, o-iodophenylamino, m-iodophenylamino, p-nitrophenylamino, o-nitrophenylamino, m-nitrophenylamino, p-carboxylphenylamino, o-carboxylphenylamino, m-carboxylphenylamino, p-carbamoylphenylamino, o-carbamoylphenylamino, m-carbamoylphenylamino, p-methoxyphenylamino, o-methoxyphenylamino, m-methoxyphenylamino, p-ethoxyphenylamino, o-ethoxyphenylamino, m-ethoxyphenylamino, p-sulfophenylamino, o-sulfophenylamino, m-sulfophenylamino, p-sulfamoylphenylamino, o-sulfamoylphenylamino, m-sulfamoylphenylamino, p-cyanoylphenylamino, o-cyanoylphenylamino, m-cyanoylphenylamino, p-hydroxymethylphenylamino, o-hydroxymethylphenylamino, m-hydroxymethylphenylamino, p-acetylphenylamino, o-acetylphenylamino, m-acetylphenylamino, p-acetaminophenylamino, o-acetaminophenylamino, m-acetaminophenylamino, p-N,N-dimethylaminophenylamino, o-N,N-dimethylaminophenylamino, m-N,N-dimethylaminophenylamino, 2-carboxyl-4-bromophenylamino, 2-carboxyl-6-chloro-phenylamino, 2-carboxyl-5-chlorophenylamino, 2-carboxyl-4-chlorophenylamino, 2-carboxyl-3-chlorophenylamino, 3-carboxyl-2-chlorophenylamino 3-carboxyl-6-chlorophenylamino, 3-carboxyl-4-chlorophenylamino, 4-carboxyl-3-chlorophenylamino, 2-cyano-5-chlorophenylamino, 2-hydroxymethyl-4-chlorophenylamino, 4-carboxyl-5-methoxy-2-chlorophenylamino, 2-sulfo-4-methyl-5-chlorophenylamino, 2-methyl-4-nitro-5-chlorophenylamino, 2-carboxyl-4,6-dichlorophenylamino, 2-carboxyl-4,6-diiodophenylamino, 4-carboxyl-2,6-diiodophenylamino, 2-carboxyl-4,6-dimethoxyphenylamino, 2-cyano-4,6-dimethoxyphenylamino, 4-carbamoyl-2,6-dinitrophenylamino, 2-carboxyl-5-fluorophenylamino, 2-carboxyl-4-fluorophenylamino, 2-carboxyl-3-fluorophenylamino, 2-cyano-3-fluorophenylamino, 2-carboxyl-4-iodophenylamino, 2-carboxyl-6-methoxyphenylamino, 3-carboxyl-6-methoxyphenylamino, 4-carboxyl-6-methoxyphenylamino, 2-carboxyl-4-methylphenylamino, 2-carboxyl-3-methylphenylamino, 3-carboxyl-2-methylphenylamino, 4-carboxyl-2-methylphenylamino, 5-carboxyl-2-methylphenylamino, 2-cyano-5-methylphenylamino, 2-hydroxymethyl-6-methylphenylamino, 2-hydroxymethyl-4-methylphenylamino, 2-methyl-3-hydroxymethylphenylamino, 2-methyl-5-hydroxymethylphenylamino, 2-cyano-4-nitrophenylamino, 4-cyano-2-nitrophenylamino, 2-methyl-4-nitrophenylamino, 2-hydroxy-3-carboxylphenylamino, 3-hydroxy-4-carboxylphenylamino, 3-carboxyl-4-hydroxyphenylamino, 4-sulfo-2-methylphenylamino, 3-sulfo-4-methylphenylamino, 2-sulfo-4-methylphenylamino, phenylthio, p-methylphenylthio, o-methylphenylthio, m-methylphenylthio, 2-carboxylphenylthio, pyridin-2-amino, pyridin-3-amino, pyridin-4-amino-5-bromopyridin-2-amino, 5-bromo-3-nitropyridin-2-amino, 4-methyl-3-nitropyridin-2-amino, 4-methyl-5-nitropyridin-2-amino, 3-nitropyridin-2-amino, 5-nitropyridin-2-amino, 3-methylpyridin-2-amino, 4-methylpyridin-2-amino, 5-methylpyridin-2-amino, 6-methylpyridin-2-amino, 4,6-dimethylpyridin-2-amino, 2-methoxypyridin-5-amino, 5-chloropyridin-2-amino, 2-chloropyridin-3-amino, 2-chloropyridin-5-amino, 3,5-dibromopyridin-2-amino, 3,5-dichloropyridin-2-amino, 4-methyl-3-nitropyridin-2-amino, 4-methyl-5-nitropyridin-2-amino, nicotinamid-6-amino, nicotinamid-2-amino, pyrimidin-2-amino, pyrimidin-4-amino, 5-bromopyrimidin-2-amino, 2,6-dihydroxypyrimidin-4-amino, 4,6-dimethoxypyrimidin-3-amino, 4,6-dimethoxypyrimidin-2-amino, 4-hydroxy-6-methylpyrimidin-2-amino, 3-hydroxypyrimidin-2-amino, 4-methoxy-5-methylpyrimidin-2-amino, 2-methoxypyrimidin-5-amino, 4-chloro-6-methylpyrimidin-2-amino, 6-chloro-2-methylthiopyrimidin-4-amino, 4,6-dichloropyrimidin-2-amino, 4,6-dichloropyrimidin-5-amino, 4-methylpyrimidin-2-amino, 3-nitropyrimidin-2-amino and 5-nitropyrimidin-2-amino.

The pharmaceutical compositions of the present invention may be formulated for oral administration in forms of tablet, capsule, sugar pill and other similar press-shaped forms, and 20-100 mg of the compounds of the present invention per unit dose may be used. The compositions of the present invention may be formulated for parenteral administration, in which 10-50 mg/ml of the compounds of the present invention may be used. The pharmaceutical compositions of the present invention for parenteral administration may be administered via skin, nasal, vagina, recta, muscle, tendon sheath, vena, or artery. Therefore, the pharmaceutical compositions of the present invention can be formulated into various forms, such as a tablet, a pill, an aerosol, a powder, an elixir, a suspension, an emulsion, syrup, soft or hard-shelled gelatin capsules, a suppository, a sterile solution for injection, or a sterile packed powder, without limitation.

The pharmaceutical compositions of the present invention may be prepared by mixing the active ingredients with pharmaceutically acceptable excipients, diluted with the excipients, or encapsulated into a carrier to form a capsule or a vesicle. As a diluent, the excipient can be provided in solid, semisolid, or liquid form as a media for the excipient, the carrier or the active ingredient. Preferred solid excipients include, but are not limited to, sugars, such as lactose, glucose, sucrose, sorbitol, mannitol, starch, and acacia; celluloses, such as methyl cellulose and microcrystalline cellulose; calcium silicate; poly-vinylpyrrolidone; magnesium stearate; sodium stearate, glycerol minostearate, etc. The liquid and semisolid excipients include, but are not limited to, water, glucose solution, saline, syrup, ethanol, glycerol, propylene glycol and all kinds of oil, including petroleum, oil that comes from animals or plants, composed oils, for example, peanut oil, soy oil, mineral oil or sesame oil. The pharmaceutical compositions of the present invention may contain pharmaceutical suitable additives, such as a lubricant, wetting agent, emulsifier, suspension agent, preservative, flavoring agent, etc.

The amount of the compounds comprised in the pharmaceutical composition of the present invention varies depending on the kind of pharmaceutical form, amount of unit dosage, the kind of excipient, and other factors known by, those skilled in the art. Furthermore, the actual dose and schedule can vary depending on whether the compositions are administered in combination with other pharmaceutical compositions, or depending on individual differences in pharmacokinetics, distribution and metabolism. Generally, when the pharmaceutical compositions of the present invention are administered orally, 20-100 mg of the compounds of the present invention per unit dose may be used. When the pharmaceutical compositions of the present invention are administered parenterally, 10-50 mg/mL of the compounds of the present invention per unit dose may be used.

The pharmaceutical compositions of the present invention can be prepared in any known methods in the pharmaceutical field, which are described in, for example, Remington's Pharmaceutical Sciences, Mark Publishing Co., Easton, Pa. 1985, herein incorporated by reference.

In the present invention, the compound as shown in formula I can be applied to prepare a pharmaceutical composition that can selectively inhibit COX-2.

A method of selectively inhibiting COX-2 is provided in the present invention in which a suitable dosage of the compounds as shown in formula I can be administered to mammals. Wherein said suitable dosage will range from about 50 to 100 mg per kilogram of body weight. Wherein said mammals include, but are not limited to, humans, cats, canines, swines, sheeps, bovines, horses, etc. The dosage will be determined by a physician or pharmaceutist, based on a variety of factors including the age, weight, condition, general health of the mammals being treated, and the curative effects to be achieved. Preferably, the total daily dosage is 50-300 mg and may be administered a single time or multiple times per day.

SPECIFIC EMBODIMENTS

Figure 1:
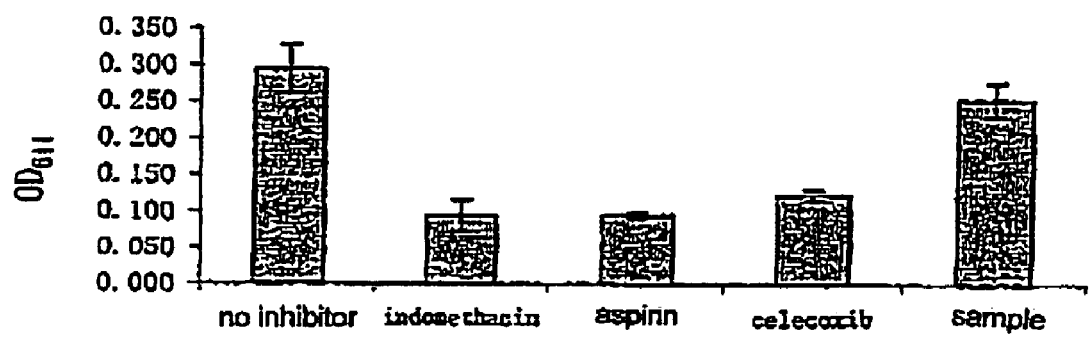
FIG. 1 indicates that a specific compound in the present invention, 5,6-di(m-acetylphenylamino)-2,3-pyridindione (sample), has almost no inhibition effect on COX-1, whereas all of the three positive controls have much higher inhibition effects.

The present invention is further described in detail by way of examples of chemical and biological experiments. These examples are illustrative and are not intended to limit the scope of the invention in any manner. The scope of the present invention is defined in the CLAIMS.

EXAMPLE 1

Synthesis of 5,6-diphenylamino-2,3-pyridindione

Method 1: 2,3-dihydroxypyridine (0.0027 mol), aniline (0.0054 mol), and $NaIO_3$ (0.0009 mol) were dissolved in 160 ml water/acetone (80:1, v/v) solvent. The reaction mixture was stirred for 2 hours, and maintained still overnight. Product was then filtered and recrystallized with petroleum ether. 5,6-diphenylamino-2,3-pyridindione can then be obtained in a brown yellow powder. The yield was 25%-45%.

Method 2: 2,3-dihydroxypyridine in Method 1 was substituted with 2,3-dihydroxy-5-bromopyridine, whereas other steps remained the same as in Method 1. The same product can be obtained, and the yield was 35%-50%.

Method 3: 30 g of immobilized polyphenol oxidase (polyphenol oxidase was extracted from potatoes, and immobilized by using the method known by those skilled in the art, the enzyme activity was 320 U/g) was added into 100 mL phosphate buffer (pH 6.8), then the mixture was gently stirred at room temperature while adding 2,3-dihydroxypyridine (0.005 mol) and aniline (0.010 mol). After stirring for 2 hours, the mixture was maintained still overnight. It was then filtered and recrystallized with petroleum ether. The final product was 5,6-disubstituted-2,3-pyridindione, and the yield was 20%-35%.

The products were analyzed by $H^1$ NMR spectroscopy, infrared spectroscopy, UV spectroscopy, mass spectroscopy, and elemental analysis. The data are as shown below:

$C_{17}H_{13}N_3O_2$, calculated value: C, 70.10%; H, 4.47%; N, 14.43%. Measured value: C, 70.24%; H, 4.36%; N, 14.39%. UV: λmax, ε(methanol): 233, 10568; 270, 9882; 399, 7580. ν(KBr): 3310, 3212, 3057, 1721, 1658, 1581, 1518, 1447 $cm^{-1}$. $^1HNMR(DMSO-d_6$, 90 MHz): δ 10.44(1H, s, N—H), 9.47(1H, s, N—H), 7.41-6.96(10H, m, Ph-H), 5.99(1H, s, C4-H)ppm. FAB MS: m/z 292($M^+$+1).

EXAMPLE 2

Synthesis of 5-phenylamino-6-(o-chlorophenylamino)-2,3-pyridindione and 6-phenylamino-5-(o-chlorophenylamino)-2,3-pyridindione 2,3-dihydroxypyridine (0.0027 mol), aniline (0.0027 mol), o-chloroaniline (0.0027 mol) and $NaIO_3$ (0.0009 mol) were dissolved in 160 ml water/acetone (80:1, v/v) solvent. The reaction mixture was stirred for 2 hours, and maintained still overnight. 5-phenylamino-6-(o-chlorophenylamino)-2,3-pyridindione and 6-phenylamino-5-(o-chlorophenylamino)-2,3-pyridindione were purified by passing the filtered product mixture through a silica gel column (100-200 mesh). The yield was 8%-15%. 5,6-diphenylamino-2,3-pyridindione and 5,6-di(o-chlorophenylamino)-2,3-pyridindione can also be obtained.

The products were analyzed by $H^1$ NMR spectroscopy, infrared spectroscopy, UV spectroscopy, mass spectroscopy, and elemental analysis.

EXAMPLE 3

Synthesis of 5-p-methoxyphenylamino-6-(p-sulfoaminophenylamino)-2,3-pyridindione and 6-p-methoxyphenylamino-5-(p-sulfoaminophenylamino)-2,3-pyridindione 2,3-dihydroxypyridine (0.0021 Mol), p-methoxyaniline (0.0027 mol), p-sulfoaminoaniline (0.0027 mol) and $NaIO_3$ (0.0009 mol) were dissolved in 160 ml of water/acetone (80:1, v/v) solvent. The reaction mixture was stirred for 4 hours, and maintained still overnight. 5-p-methoxyphenylamino-6-(p-sulfoaminophenylamino)-2,3-pyridindione and 6-p-methoxyphenylamino-5-(p-sulfoaminophenylamino)-2,3-pyridindione were purified by passing the filtered reaction mixture through a silica gel column (100-200 mesh). The yield was 12%-16%. 5,6-di(p-methoxyphenylamino)-2,3-pyridindione and 5,6-di(p-sulfoaminophenylamino)-2,3-pyridindione can also be obtained.

The products were analyzed by $H^1$ NMR spectroscopy, infrared spectroscopy, UV spectroscopy, mass spectroscopy, and elemental analysis.

EXAMPLE 4

Synthesis of 5,6-di(p-chlorophenylamino)-2,3-pyridindione 2,3-dihydroxypyridine (0.0027 mol), p-chloroaniline (0.0054 mol), and $NaIO_3$ (0.0009 mol) were dissolved in 160 ml water/acetone (80:1, v/v) solvent. The reaction mixture was stirred for 2 hours, and maintained still overnight. It was then filtered and recrystallized with chloroform. The final product was 5,6-di(p-chlorophenylamino)-2,3-pyridindione in a yellow powder. The yield was 42%-60%.

The products were analyzed by $H^1$ NMR spectroscopy, infrared spectroscopy, UV spectroscopy, mass spectroscopy, and elemental analysis. The data are as shown below:

$C_{17}H_{11}N_3O_2Cl_2$, calculated value: C, 56.67%; H, 3.06%; N, 11.67%. Measured value: C, 56.76%; H, 3.04%; N, 11.56%. UV: $\lambda max$, $\epsilon$ (methanol): 211,5931; 237,7119; 278,3722. $\nu$(KBr): 3268, 3029, 2924, 2860, 1721, 1658, 1595 $cm^{-1}$. $^1$HNMR (DMSO-$d_6$, 90 MHz):$\delta$ 10.91(1H, s, N—H), 9.62(1H, s, N—H), 7.47(4H, d, J=4.9 Hz, Ph-H), 7.05(41, d, J=5.6 Hz, Ph-H), 6.01(1H, s, C4-H)ppm. FAD MS: m/z 360 ($M^+$).

EXAMPLE 5

Synthesis of 5,6-di(p-methoxyphenylamino)-2,3-pyridindione 2,3-dihydroxypyridine (0.0027 mol), p-methoxyaniline (0.0054 mol); and $NaIO_3$ (0.0009 mol) were dissolved in 160 ml of water/acetone (80:1, v/v) solvent. The reaction mixture was stirred for 2 hours, and maintained still overnight. It was then filtered, and recrystallized with chloroform. The final product was 5,6-di(p-methoxyphenylamino)-2,3-pyridindione in a red powder. The yield was 32%-50%.

The products were analyzed by $H^1$ NMR spectroscopy, infrared spectroscopy, UV spectroscopy, mass spectroscopy, and elemental analysis. The data are as shown below:

$C_{19}H_{17}N_3O_4$, calculated value: C, 64.96%; H, 4.84%; N, 11.96%. Measured value: C, 64.73%; H, 4.80%; N, 11.75%. UV: $\lambda max$, $\epsilon$ (methanol): 229,12283; 273,8750; 405,5971. $\nu$(KBr):3268, 2938, 2839, 1714, 1651, 1581, 1519, 1461 $cm^{-1}$. $^1$HNMR (DMSO-$d_6$, 90 MHz):$\delta$ 10.42(1H, br, N—H), 9.46(1H, s, N—H), 7.35(2H, d, J=6.0 Hz, Ph-H), 7.05(6H, d, J=5.6 Hz, Ph-H), 5.82(1H, s, C4-H), 3.78(6H, s, ($C_6H_4$)—$OCH_3$)ppm. FAB MS: m/z 352($M^+$+1).

EXAMPLE 6

Synthesis of 5,6-di(m-chlorophenylamino)-2,3-pyridindione 2,3-dihydroxypyridine (0.0027 mol), m-chloroaniline (0.0054 mol), and $NaIO_3$ (0.0009 mol) were dissolved in 160 ml of water/acetone (80:1, v/v) solvent. The reaction mixture was stirred for 2 hours, and maintained still overnight. It was then filtered and recrystallized with chloroform. The final product was 5,6-di(m-chlorophenylamino)-2,3-pyridindione in a yellow powder. The yield was 36%-57%.

The products were analyzed by $H^1$ NMR spectroscopy, infrared spectroscopy, UV spectroscopy, mass spectroscopy, and elemental analysis. The data are as shown below:

$C_{17}H_{11}N_3O_2Cl_2$, calculated value: C, 56.67%; H, 3.06%; N, 11.67%. Measured value: C, 56.76%; H, 3.04%; N, 11.56%. UV: $\lambda max$, $\epsilon$ (methanol): 217,7740; 238,7121; 396, 4577. $\nu$(KBr):3226, 3064, 2853, 1721, 1658, 1602, 1581, 1518, 1475 $cm^{-1}$. $^1$HNMR (DMSO-$d_6$, 90 MHz):$\delta$ 10.99(1H, s, N—H), 9.58(1H, s, N—H), 7.42-6.90(8H, m, Ph-H), 6.05 (1H, s, C4-H)ppm. FAB MS: m/z 360($M^+$).

EXAMPLE 7

Synthesis of 5,6-di(o-tolylamino)-2,3-pyridindione 2,3-dihydroxypyridine (0.0027 mol), o-methylaniline (0.0054 mol), and $NaIO_3$ (0.0009 mol) were dissolved in 160 ml of water/acetone (80:1, v/v) solvent. The reaction mixture was stirred for 2 hours, and maintained still overnight. It was then filtered and recrystallized with chloroform. The final product was 5,6-di(o-tolylamino)-2,3-pyridindione in a red powder. The yield was 27%-45%.

The products were analyzed by $H^1$ NMR spectroscopy, infrared spectroscopy, UV spectroscopy, mass spectroscopy, and elemental analysis. The data are as shown below:

$C_{19}H_{17}N_3O_2$, calculated value: C, 71.47%; H, 5.33%; N, 13.17%. Measured value: C, 71.59%; H, 5.37%; N, 13.25%. UV: $\lambda max$, $\epsilon$ (methanol): 226,5064; 270,4621; 388,2975. $\nu$(KBr):3282, 3057, 2917, 2853, 1721, 1651, 1518, 1510 $cm^{-1}$. $^1$HNMR (DMSO-$d_6$, 90 MHz):$\delta$ 10.54(1H, s, N—H), 9.40(1H, s, N—H), 7.31-6.92(8H, m, Ph-H), 5.37(1H, s, C4-H), 2.20(6H, s, ($C_6H_4$)—$CH_3$)ppm. FAD MS: m/z 320 ($M^{+b+1}$).

EXAMPLE 8

Synthesis of 5,6-di(p-tolylamino)-2,3-pyridindione 2,3-dihydroxypyridine (0.0027 mol), p-methylaniline (0.0054 mol), and $NaIO_3$ (0.0009 mol) were dissolved in 160 ml water/acetone (80:1, v/v) solvent. The reaction mixture was stirred for 2 hours; and maintained still overnight. It was then filtered and recrystallized with chloroform. The final product was 5,6-di(p-tolylamino)-2,3-pyridindione in a red powder. The yield was 32%-54%.

The products were analyzed by $H^1$ NMR spectroscopy, infrared spectroscopy, UV spectroscopy, mass spectroscopy, and elemental analysis. The data are as shown below:

$C_{19}H_{17}N_3O_2$, calculated value: C, 71.47%; H, 5.33%; N, 13.17%. Measured value: C, 71.15%; H, 5.29%; N, 13.19%. UV. λmax, ε (methanol): 212,10750; 231,11261; 276,8773; 399,6552. ν(KBr):3353, 3261, 3128, 2860, 1721, 1658, 1609, 1518, 1526 cm$^{-1}$. $^1$HNMR (DMSO-$d_6$, 90 MHz):δ 10.27(1H, s, N—H), 9.38 (1H, s, N—H), 7.26(4H, d, J=4.9 Hz, Ph-H), 6.95(4H, d, J=5.1 Hz, Ph-H), 5.93(1H, s, C4-H), 2.33(6H, s, ($C_6H_4$)—$CH_3$)ppm. FAB MS: m/z 320($M^+$+1).

EXAMPLE 9

Synthesis of 5-p-acetylphenylamino-6-phenylamino-2,3-pyridindione 2,3-dihydroxypyridine (0.0027 mol), aniline (0.0027 mol), p-acetylaniline (0.0027 mol), and $NaIO_3$ (0.0009 mol) were dissolved in 160 ml water/acetone (80:1, v/v) solvent. The reaction mixture was stirred for 2 hours, and maintained still overnight. The product mixture was filtered, and passed through a silica gel column (200-400 mesh). The final product was 5-p-acetylphenylamino-6-phenylamino-2,3-pyridindione in yellow powder. The yield was 23%-45%. 5,6-diphenylamino-2,3-pyridindione can also be obtained.

The products were analyzed by $H^1$ NMR spectroscopy, infrared spectroscopy, UV spectroscopy, mass spectroscopy, and elemental analysis The data are as shown below:

$C_{19}H_{15}N_3O_3$, calculated value: C, 68.47%; H, 4.50%; N, 12.61%. Measured value: C, 68.95%; H, 4.36%; N, 12.36%. UV: λmax, ε (methanol): 207, 2529; 284, 2983; 404, 1037. ν(KBr):3402, 3177, 3057, 1721, 1672, 15741, 1518 cm$^{-1}$. $^1$HNMR (DMSO-$d_6$, 90 MHz):δ 10.87(1H, s, N—H), 9.62 (1H, s, N—H), 8.07-6.94(9H, m, Ph-H), 6.26(1H, s, C4-H), 2.57(3H, s, ($C_6H_4$)—$CH_3$)ppm. FAB MS: m/z 334($M^+$+1).

The rest of the compounds in the present invention: may be prepared with the corresponding reactants by using the methods described in Examples 1-9.

Experimental Test 1

Inhibition of COX-1 with 5,6-di(m-acetylphenylamino)-2,3-pyridindione

Materials: 0.1 M Tris HCl buffer (pH 8.0, containing 0.5 μM hemachrome), tetramethylparaphenylenediamine dihydrochloride (TMPD 17 mM), arachidonic acid (A.A. 10 mM, in anhydrous ethanol), COX-1 (0.50 μg/ml, 23833 u/ml). Inhibitors: aspirin (10 mM, in dimethylsulfoxide), indomethacin (10 mM, in dimethylsulfoxide), celecoxib (10 mM, in dimethylsulfoxide), 5,6-di(m-acetylphenylamino)-2,3-pyridindione (10 mM, in dimethylsulfoxide).

Methods: 4 μl of COX-1 was added to 960 μl 0.1 M Tris-HCl in a cell. The mixture was equilibrated for 30s, and then added with 1 μl inhibitor. After 2 min, 15 μl TMPD and 15 μl A.A. were immediately added to the mixture and mixed well. After 7 min, the absorption was measured at 611 nm.

Results are shown in FIG. 1. FIG. 1 indicates that the activity of COX-4 was inhibited by inhibitors aspirin, celecoxib, and indomethacin. Compared with the control group without inhibitors, the compound of the present invention has no obvious inhibition effects.

Experimental Test 2

Inhibition of COX-2 with 5,6-di(m-acetylphenylamino)-2,3-pyridindione.

Materials: COLO 205 cell line (stored at −80° C., purchased from Cayman Chemical Company(U.S.A.)), 1× trypsin-EDTA, RPMI medium 1640(with 25 mM HEPES and L-glutamine, 10% calf serum, 2% penicillin and streptomycin), phosphate buffer 1× PBS)(This buffer is obtained by mixing up NaCl 8 g, KCl 0.2 g, $Na_2HPO_4$ 1.44 g, $KH_2PO_4$ 0.24 g, adding water to 800 ml, adjusting pH to 7.4, and adding water to 1 L. The buffer was sterilized and stored at room temperature), freeze medium (RPMI medium 1640, with 25 mM HEPES and L-glutamine; 10% DMSO). Enzyme-Linked ImmunoSorbent Assay Kit (Prostaglandins E2 (PEG2) EIA Kit-Monoclonal, Cayman Chemical company (U.S.A)).

Methods: Cell cultures were grown according to Laboratory Manual of Cell Biology, edited by D. O. Hall and Shirley E. Hawkins, Crane, Russak & Co., 1975; ELISA was carried out according to the instruction of Prostaglandins E2 (PEG2) EIA Kit-Monoclonal, No. 514010, Cayman Chemical Company (U.S.A).

Figure 2:
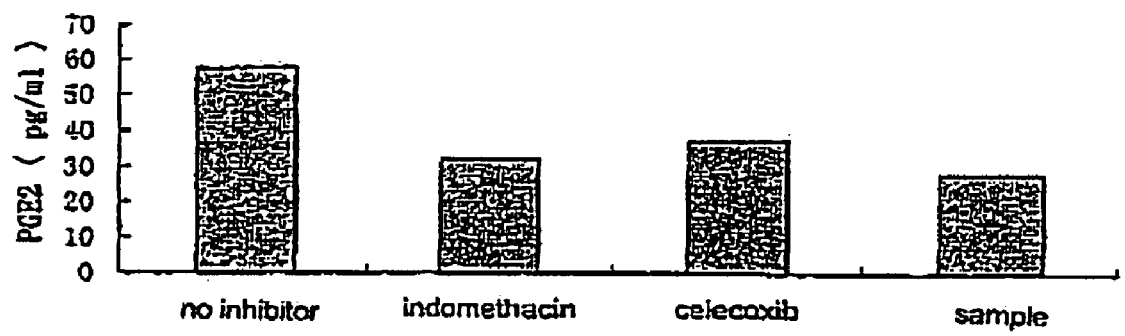
FIG. 2 shows that the compound in the present invention, 5,6-di(m-acetylphenylamino)-2,3-pyridindione (sample), inhibits the growth of the COLO205 cells ex vivo, whereas both of the two positive controls have lower inhibition effects than the compound.

Results are shown in FIG. 2. FIG. 2 indicates that the activity of COX-2 was inhibited not only by its inhibitors, celecoxib and indomethacin, but also by the compound of the present invention, whereas the latter one has higher inhibition effects on COX-2 than the former two.

Experimental Test 3

Effects of 5,6-di(m-acetylphenylamino)-2,3-pyridindione and 5,6-di(m-carboxylphenylamino)-2,3-pyridindione on a rat model of toe swelling.

Forty healthy male rats were divided randomly into 4 groups, 10 rats per group, namely, the blank control group, the 5,6-di(m-acetylphenylamino)-2,3-pyridindione group, the 5,6-di(m-carboxylphenylamino)-2,3-pyridindione group, and the aspirin group as the drug control group. 0.1 ml of inflammation inducer (3% formaldehyde) was subcutaneously injected into the right toe of the hind leg of each rat. After 24 hours, the compounds with dosage listed in Table 1 were injected into the rats, respectively. The volume of the toes was measured 2 hours later after injection by using the Water Volume Method described in the Methodology of Pharmacology Experiments, 2nd edition, Shu-yun Xu, etc., People's Medical Publishing House, Beijing, 1991. The inhibition rates for each group were calculated based on the toe, volume in the blank control group, as listed in Table 1.

TABLE 1

| Group | Dosage (mg/kg) | Inhibition rate (%) |
|---|---|---|
| Blank control | 0 | 0 |
| 5,6-di(m-acetylphenylamino)-2,3-pyridindione | 5 | 62.5 |
| 5,6-di(m-carboxylphenylamino)-2,3-pyridindione | 5 | 45.5 |
| Aspirin | 50 | 10.1 |

Experimental Test 4

Effects of 5,6-di(m-acetylphenylamino)-2,3-pyridindione and 5,6-di(m-carboxylphenylamino)-2,3-pyridindione on a mouse model of auricle swelling.

Forty healthy male mice were divided randomly into 4 groups, 10 mice per group, namely, the blank control group, the 5,6-di(m-acetylphenylamino)-2,3-pyridindione group, the 5,6-di(m-carboxylphenylamino)-2,3-pyridindione group, and the aspirin group as the drug control group. The compounds with dosage listed in Table 2 were administered orally to the rats, respectively. After 60 min 0.05 ml xylene (analytical grade) was applied on the right ear of each mouse, respectively. The mice were killed 4 hours later, a disk of ear tissue was removed from the same location of both ears using a 5.5-mm biopsy punch, then each of the ear disks was weighed, and the rates of auricle swelling inhibition were calculated, as listed in Table 2.

TABLE 2

| Group | Dosage (mg/kg) | Inhibition rate (%) |
|---|---|---|
| Blank control | 0 | 0 |
| 5,6-di(m-acetylphenylamino)-2,3-pyridindione | 30 | 83.2 |
| 5,6-di(m-carboxylphenylamino)-2,3-pyridindione | 30 | 65.5 |
| Aspirin | 100 | 30.1 |

Experimental Test 6

Toxicological test of 5,6-di(m-acetylphenylamino)-2,3-pyridindione Single dose administration was used. 5,6-di(m-acetylphenylamino)-2,3-pyridindione was prepared to the required concentration with the presence of 0.5% DMSO. Sixty healthy male mice and 60 healthy female mice were divided randomly into 10 mice per group, 12 groups, among which 5 groups were administered by tail vein injection, and 5 groups were administered via gastro infusion, and the other two groups were used as negative controls. The activities and death of mice were observed and recorded for 7 days after the administration of the compound. No death of the animals was observed and the toxic reaction, in aspect of activity, reactivity, back hair, dejecta, etc., was normal during the tests. See Table 4 for results.

TABLE 4

| Tail vein injection | | | | Gastro infusion | | | |
|---|---|---|---|---|---|---|---|
| Dosage (mg/kg) | No.(animal) | Death rate | Toxic reaction | Dosage (mg/kg) | No.(animal) | Death rate | Toxic reaction |
| 3000 | 10 | 0 | normal | 3000 | 10 | 0 | normal |
| 2100 | 10 | 0 | normal | 2100 | 10 | 0 | normal |
| 1470 | 10 | 0 | normal | 1470 | 10 | 0 | normal |
| 1030 | 10 | 0 | normal | 1030 | 10 | 0 | normal |
| 720 | 10 | 0 | normal | 720 | 10 | 0 | normal |
| 0 | 10 | 0 | normal | 0 | 10 | 0 | normal |

Experimental Test 5

Effects of 5,6-di(m-acetylphenylamino)-2,3-pyridindione and 5,6-di(m-carboxylphenylamino)-2,3-pyridindione on an animal model of anti-histamine.

Forty healthy male rats were divided randomly into 4 groups, 1.0 rats per group, namely, the blank control group, the 5,6-di(m-acetylphenylamino)-2,3-pyridindione group, the 5,6-di(m-carboxylphenylamino)-2,3-pyridindione group, and the aspirin group as the positive control group. The compounds with dosage listed in Table 3 were administered orally to the rats, respectively, then 0.1 ml of µg/ml histamine was administered subcutaneously, and then 1 ml of 1% Evans blue was immediately injected intravenously under the tongue. The rats were killed 15 min later, the dyed back skin was removed, broken up, and incubated in water/acetone (3:7, v/v) solution for 48 hours, the solution was then filtered, measured with a spectrophotometer, and the inhibition rates based on the dyed area were calculated.

TABLE 3

| Group | Dosage (mg/kg) | Absorbency(A) | Inhibition rate (%) |
|---|---|---|---|
| Blank control | 0 | 0.099 | 0 |
| 5,6-di(m-acetylphenylamino)-2,3-pyridindione | 10 | 0.081 | 19 |
| 5,6-di(m-carboxylphenylamino)-2,3-pyridindione | 10 | 0.084 | 16 |
| Aspirin | 160 | 0.086 | 13 |

Experimental Test 7

Effects of 5 compound samples, including 5,6-di(m-acetylphenylamino)-2,3-pyridindione, on the increment of the mouse skin capillary permeability One hundred and seventy healthy male mice were divided randomly into 17 groups, 10 mice per group, namely, the blank control group, the high, medium, and low dosage groups of 5,6-di(m-acetylphenylamino)-2,3-pyridindione, respectively, the high, medium, and low dosage groups of 5,6-di(m-carboxylphenylamino)-2,3-pyridindione, respectively, the high, medium, and low dosage groups of 5,6-di(p-carboxylphenylamino)-2,3-pyridindione, respectively, the high, medium, and low dosage groups of 5,6-di(p-chlorophenylamino)-2,3-pyridindione, respectively, the high, medium, and low dosage groups of 5,6-di(p-tolylamino)-2,3-pyridindione, and the aspirin group as the positive control group. The mice were administered via gastro infusion according to the Table 5, and 1 hour later, 0.5% Evans blue saline was injected into the mice via tail vain at 0.1 ml/10 g, then xylene with a dosage of 0.03 ml/mouse was applied to the mice in the shaved area at the middle belly. The mice were killed by cervical dislocation 20 min later, and their belly skin was peeled off, where the blue area was removed by using a biopsy punch, broken up by using surgery scissors, and put into covered glass tubes. Seven milliliters of acetone/water (7:3, v/v) solution was added into each tube, which was then stored in the dark and was gently shaken up 2-3 times daily. After 3 days, the solution in each tube was centrifuged at 2000 rpm for 10 min, and the supernatant was measured for optical density at 590 nm with the absorption of acetone/water (7:3, v/v) solution as the baseline. The lower the OD value, the better the anti-inflammatory effect.

TABLE 5

| Group | Dosage (mg/kg) | OD (A) |
|---|---|---|
| 0.5% CMC-Na (blank control) | 0.4 ml/mouse | 0.442 ± 0.240 |
| Aspirin Enteric-coated Tablet | 6.5 | 0.198 ± 0.190 |
| 5,6-di(m-acetylphenylamino)-2,3-pyridindione | | |
| Low dosage | 1.0 | 0.241 ± 0.121 |
| Medium dosage | 3.2 | 0.035 ± 0.049 |
| High dosage | 6.5 | 0.019 ± 0.018 |
| 5,6-di(m-carboxylphenyl amino)-2,3-pyridindione | | |
| Low dosage | 1.0 | 0.038 ± 0.026 |
| Medium dosage | 3.2 | 0.030 ± 0.010 |
| High dosage | 6.5 | 0.036 ± 0.011 |
| 5,6-di(p-carboxylphenylamino)-2,3-pyridindione | | |
| Low dosage | 1.0 | 0.089 ± 0.054 |
| Medium dosage | 3.2 | 0.043 ± 0.023 |
| High dosage | 6.5 | 0.030 ± 0.012 |
| 5,6-di(p-chlorophenylamino)-2,3-pyridindione | | |
| Low dosage | 1.0 | 0.142 ± 0.098 |
| Medium dosage | 3.2 | 0.035 ± 0.026 |
| High dosage | 6.5 | 0.015 ± 0.015 |
| 5,6-di(p-tolylamino)-2,3-pyridindione | | |
| Low dosage | 1.0 | 0.049 ± 0.049 |
| Medium dosage | 3.2 | 0.011 ± 0.022 |
| High dosage | 6.5 | 0.051 ± 0.042 |

The above described Experimental Tests 1 and 2 show that o-pyridinequinone derivatives in the present invention as shown in formula 1 has good inhibition effects on COX-2, but weak on COX-1, which indicates the good inhibition selectivity of those compounds on COX-2. Experimental Tests 3-5 indicate that o-pyridinequinone derivatives in the present invention as shown in formula 1 may be applied as pharmaceuticals or pharmaceutical compositions to treat inflammation. In Experimental Test 6, o-pyridinequinone derivatives in the present invention as shown in formula 1 were demonstrated as relatively safe drugs with no severe acute toxicity. As shown in Experimental Test 7, o-pyridinequinone derivatives in the present invention as shown in formula 1 have a very good anti-inflammatory effect.

What is claimed is:

1. A compound represented by formula I:

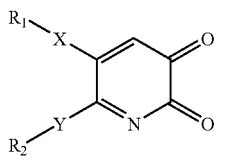

(formula I)

wherein
R$_1$ and R$_2$ may be the same or different, each independently represents substituted or unsubstituted phenyl, pyridinyl or pyrimidinyl,
X and Y may be the same or different, each independently represents an N or S atom, provided that when X or Y represents S, then the R$_1$ or R$_2$ attached to the S atom is substituted or unsubstituted phenyl.

2. The compound of claim 1, wherein:
when R$_1$ or R$_2$ represents substituted phenyl, substituted pyridinyl or substituted pyrimidinyl, the phenyl, pyridinyl, pyrimidinyl has one to three substituents independently selected from the group consisting of C$_1$-C$_6$ linear or branched alkyl, C$_1$-C$_6$ linear or branched alkoxyl, halogen, amino, di(C$_1$-C$_3$ alkyl)amino, carbamyl, sulfamoyl, sulfo, cyano, nitro, carboxyl, hydroxy, hydroxy (C$_1$-C$_3$) alkyl, (C$_1$-C$_3$ alkyl)acyl and (C$_1$-C$_3$ alkyl)thio.

3. The compound of claim 2, wherein:
R$_1$—X— and R$_2$—Y— each is independently selected from the group consisting of p-tolylamino, o-tolylamino, m-tolylamino, p-ethylphenylamino, o-ethylphenylamino, m-ethylphenylamino, p-chlorophenylamino, o-chlorophenylamino, m-chlorophenylamino, p-fluorophenylamino, o-fluorophenylamino, m-fluorophenylamino, p-bromophenylamino, o-bromophenylamino, m-bromophenylamino, p-iodophenylamino, o-iodophenylamino, m-iodophenylamino, p-nitrophenylamino, o-nitrophenylamino, m-nitrophenylamino, p-carboxylphenylamino, o-carboxylphenylamino, m-carboxylphenylamino, p-carbamoylphenylamino, o-carbamoylphenylamino, m-carbamoylphenylamino, p-methoxyphenylamino, o-methoxyphenylamino, m-methoxyphenylamino, p-ethoxyphenylamino, o-ethoxyphenylamino, m-ethoxyphenylamino, p-sulfophenylamino, o-sulfophenylamino, m-sulfophenylamino, p-sulfamoylphenylamino, o-sulfamoylphenylamino, m-sulfamoylphenylamino, p-cyanoylphenylamino, o-cyanoylphenylamino, m-cyanoylphenylamino, p-hydroxymethylphenylamino, o-hydroxymethylphenylamino, m-hydroxymethylphenylamino, p-acetylphenylamino, o-acetylphenylamino, m-acetylphenylamino, p-acetaminophenylamino, o-acetaminophenylamino, m-acetaminophenylamino, p-N,N-dimethylaminophenylamino, o-N,N-dimethylaminophenylamino, m-N,N-dimethylaminophenylamino, 2-carboxyl-4-bromophenylamino, 2-carboxyl-6-chloro-phenylamino, 2-carboxyl-5-chlorophenylamino, 2-carboxyl-4-chlorophenylamino, 2-carboxyl-3-chlorophenylamino, 3-carboxyl-2-chlorophenylamino, 3-carboxyl-6-chlorophenylamino, 3-carboxyl-4-chlorophenylamino, 4-carboxyl-3-chlorophenylamino, 2-cyano-5-chlorophenylamino, 2-hydroxymethyl-4-chlorophenylamino, 4-carboxyl-5-methoxy-2-chlorophenylamino, 2-sulfo-4-methyl-5-chlorophenylamino, 2-methyl-4-nitro-5-chlorophenylamino, 2-carboxyl-4,6-dichlorophenylamino, 2-carboxyl-4,6-diiodophenylamino, 4-carboxyl-2,6-diiodophenylamino, 2-carboxyl-4,6-dimethoxyphenylamino, 2-cyano-4,6-dimethoxyphenylamino, 4-carbamoyl-2,6-dinitrophenylamino, 2-carboxyl-5-fluorophenylamino, 2-carboxyl-4-fluorophenylamino, 2-carboxyl-3-fluorophenylamino, 2-cyano-3-fluorophenylamino, 2-carboxyl-4-iodophenylamino, 2-carboxyl-6-methoxyphenylamino, 3-carboxyl-6-methoxyphenylamino, 4-carboxyl-6-methoxyphenylamino, 2-carboxyl-4-methylphenylamino, 2-carboxyl-3-methylphenylamino, 3-carboxyl-2-methylphenylamino, 4-carboxyl-2-methylphenylamino, 5-carboxyl-2-methylphenylamino, 2-cyano-5-methylphenylamino, 2-hydroxymethyl-6-methylphenylamino, 2-hydroxymethyl-4-methylphenylamino, 2-methyl-3-hydroxymethylphenylamino, 2-methyl-5-hydroxymethylphenylamino, 2-cyano-4-nitrophenylamino, 4-cyano-2-nitrophenylamino, 2-methyl-4-nitrophenylamino, 2-hydroxy-3-carboxylphenylamino, 3-hydroxy-4-carboxylphenylamino, 3-carboxyl-4-hydroxyphenylamino, 4-sulfo-2-methylphenylamino, 3-sulfo-4-methylphenylamino, 3-sulfo-4-methylphenylamino, phenylthio, p-methylphenylthio, o-methylphenylthio, m-methylphenylthio, 2-carboxylphenylthio, pyridin-2-amino, pyridin-3-amino, pyridin-4-amino, 5-bromopyridin-2-amino, 5-bromo-3-nitropyridin-2-amino, 4-methyl-3-nitropyridin-2-amino, 4-methyl-5-nitropyridin-2-amino, 3-nitropyridin-2-amino, 5-nitropyridin-2-amino, 3-methylpyridin-2-amino, 4-methylpyridin-2-amino, 5-methylpyridin-2-amino, 6-methylpyridin-2-amino, 4,6-dimethylpyridin-2-amino, 2-methoxypyridin-5-amino, 5-chloropyridin-2-amino, 2-chloropyridin-3-amino, 2-chloropyridin-5-amino, 3,5-dibromopyridin-2-amino, 3,5-dichloropyridin-2-amino, 4-methyl-3-nitropyridin-2-amino, 4-methyl-5-nitropyridin-2-amino, nicotinamid-6-amino, nicotinamid-2-amino, pyrimidin-2-amino, pyrimidin-4-amino, 5-bromopyrimidin-2-amino, 2,6-dihydroxypyrimidin-4-amino, 4,6-dimethoxypyrimidin-3-amino, 4,6-dimethoxypyrimidin-2-amino, 4-hydroxy-6-methylpyrimidin-2-amino, 3-hydroxypyrimidin-2-amino, 4-methoxy-5-methylpyrimidin-2-amino, 2-methoxypyrimidin-5-amino, 4-chloro-6-methylpyrimidin-2-amino, 6-chloro-2-methylthiopyrimidin-4-amino, 4,6-dichloropyrimidin-2-amino, 4,6-dichloropyrimidin-5-amino, 4-methylpyrimidin-2-amino, 3-nitropyrimidin-2-amino and 5-nitropyrimidin-2-amino.

4. A method of preparing the compound represented by formula I,

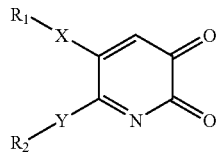

(formula I)

comprising:
reacting the compound represented by formula II

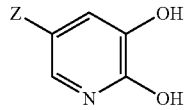

(formula II)

wherein Z is H or halogen,
with one or two aromatic amines represented by formula III R₄NH₂ (formula III)

Wherein $R_4$ represents substituted or unsubstituted phenyl, pyridinyl or pyrimidinyl, or,
with one or two thiophenols represented by formula IV R₅SH (formula IV)

Wherein $R_5$ represents substituted or unsubstituted phenyl,
in the presence of an oxidant at a temperature of 10-80° C. for 0.2-20 hrs.

5. The method of claim 4, wherein the halogen is chloro or bromo.

6. The method of claim 4, wherein $R_4$ represents substituted phenyl, substituted pyridinyl or substituted pyrimidinyl, the phenyl, pyridinyl or pyrimidinyl has one to three substituents independently selected from the group consisting of $C_1$-$C_6$ linear or branched alkyl, $C_1$-$C_6$ linear or branched alkoxyl, halogen, amino, di($C_1$-$C_3$ alkyl)amino, carbamyl, sulfamoyl, sulfo, cyano, nitro, carboxyl, hydroxy, hydroxy ($C_1$-$C_3$) alkyl, ($C_1$-$C_3$ alkyl)acyl and ($C_1$-$C_3$ alkyl)thio.

7. The method of claim 4, wherein $R_5$ represents a substituted phenyl having one to two substituents selected from the group consisting of methyl, ethyl, propyl and carboxyl.

8. The method of claim 4, wherein the reaction is performed in an aqueous organic solvent, and wherein the oxidant is selected from the group consisting of alkli metal salts of bromic acid, alkli metal salts of iodic acid, alkli metal salts of persulfuric acid, alkli metal salts of chloric acid, and the mixture thereof.

9. The method of claim 8, wherein the alkali metal is sodium or potassium.

10. The method of claim 8, wherein the reaction temperature is 40° C.-60° C.

11. The method of claim 8, wherein the oxidant is added in portions.

12. The method of claim 8, wherein the reaction time is 2-10 hrs.

13. The method of claim 4, wherein the oxidant is a polyphenoloxidase.

14. The method of claim 13, wherein the reaction temperature is 25° C.-45° C.

15. The method of claim 13, wherein the reaction time is 2-20 hrs.

16. The method of claim 4, wherein the organic solvent is selected from the group consisting of methanol, ethanol, dimethyl sulfoxide, acetone, dioxane, tetrahydrofuran, dimethyl formamide, acetonitrile, and the mixture thereof.

17. A pharmaceutical composition, which contains the compound represented by formula I as an active component and a pharmaceutically acceptable carrier,

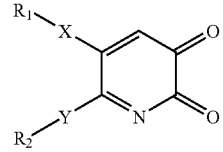

(formula I)

wherein
$R_1$ and $R_2$ may be the same or different, each independently represents substituted or unsubstituted phenyl, pyridinyl or pyrimidinyl,
X and Y may be the same or different, each independently represents an N or S atom, provided that when X or Y represents S, then the $R_1$ or $R_2$ attached to the S atom is substituted or unsubstituted phenyl.

18. The pharmaceutical composition of claim 17, wherein when $R_1$ or $R_2$ represents substituted phenyl, substituted pyridinyl or substituted pyrimidinyl, the phenyl, pyridinyl, pyrimidinyl has one to three substituents independently selected from the group consisting of $C_1$-$C_6$ linear or branched alkyl, $C_1$-$C_6$ linear or branched alkoxyl, halogen, amino, di($C_1$-$C_3$ alkyl)amino, carbamyl, sulfamoyl, sulfo, cyano, nitro, carboxyl, hydroxy, hydroxy($C_1$-$C_3$) alkyl, ($C_1$-$C_3$ alkyl)acyl and ($C_1$-$C_3$ alkyl)thio.

19. The pharmaceutical composition of claim 18, wherein $R_1$—X— and $R_2$—Y— each is independently selected from the group consisting of p-tolylamino, o-tolylamino, m-tolylamino, p-ethylphenylamino, o-ethylphenylamino, m-ethylphenylamino, p-chlorophenylamino, o-chlorophenylamino, m-chlorophenylamino, p-fluorophenylamino, o-fluorophenylamino, m-fluorophenylamino, p-bromophenylamino, o-bromophenylamino, m-bromophenylamino, p-iodophenylamino, o-iodophenylamino, m-iodophenylamino, p-nitrophenylamino, o-nitrophenylamino, m-nitrophenylamino, p-carboxylphenylamino, o-carboxylphenylamino, m-carboxylphenylamino, p-carbamoylphenylamino, o-carbamoylphenylamino, m-carbamoylphenylamino, p-methoxyphenylamino, o-methoxyphenylamino, m-methoxyphenylamino, p-ethoxyphenylamino, o-ethoxyphenylamino, m-ethoxyphenylamino, p-sulfophenylamino, o-sulfophenylamino, m-sulfophenylamino, p-sulfamoylphenylamino, o-sulfamoylphenylamino, m-sulfamoylphenylamino, p-cyanoylphenylamino, o-cyanoylphenylamino, m-cyanoylphenylamino, p-hydroxymethylphenylamino, o-hydroxymethylphenylamino, m-hydroxymethylphenylamino, p-acetylphenylamino, o-acetylphenylamino, m-acetylphenylamino, p-acetaminophenylamino, o-acetaminophenylamino, m-acetaminophenylamino, p-N,N-dimethylaminophenylamino, o-N,N-dimethylaminophenylamino, m-N,N-dimethylaminophenylamino, 2-carboxyl-4-bromophenylamino, 2-carboxyl-6-chloro-phenylamino, 2-carboxyl-5-chlorophenylamino, 2-carboxyl-4-chlorophenylamino, 2-carboxyl-3-chlorophenylamino, 3-carboxyl-2-chlorophenylamino, 3-carboxyl-6-chlorophenylamino, 3-carboxyl-4-chlorophenylamino, 4-carboxyl-3-chlorophenylamino, 2-cyano-5-chlorophenylamino, 2-hydroxymethyl-4-chlorophenylamino, 4-carboxyl-5-methoxy-2-chlorophenylamino, 2-sulfo-4-methyl-5-chlorophenylamino, 2-methyl-4-nitro-5-chlorophenylamino, 2-carboxyl-4,6-dichlorophenylamino, 2-carboxyl-4,6-diiodophenylamino, 4-carboxyl-2,6-diiodophenylamino, 2-carboxyl-4,6-dimethoxyphenylamino, 2-cyano-4,6-dimethoxyphenylamino, 4-carbamoyl-2,6-dinitrophenylamino, 2-carboxyl-5-fluorophenylamino, 2-carboxyl-4-fluorophenylamino, 2-carboxyl-3-fluorophenylamino, 2-cyano-3-fluorophenylamino, 2-carboxyl-4-iodophenylamino, 2-carboxyl-6-methoxyphenylamino, 3-carboxyl-6-methoxyphenylamino, 4-carboxyl-6-methoxyphenylamino, 2-carboxyl-4-methylphenylamino, 2-carboxyl-3-methylphenylamino, 3-carboxyl-2-methylphenylamino, 4-carboxyl-2-methylphenylamino, 5-carboxyl-2-methylphenylamino, 2-cyano-5-methylphenylamino, 2-hydroxymethyl-6-methylphenylamino, 2-hydroxymethyl-4-methylphenylamino, 2-methyl-3-hydroxymethylphenylamino, 2-methyl-5-hydroxymethylphenylamino, 2-cyano-4-nitrophenylamino, 4-cyano-2-nitrophenylamino, 2-methyl-4-nitrophenylamino, 2-hydroxy-3-carboxylphenylamino, 3-hydroxy-4-carboxylphenylamino, 3-carboxyl-4-hydroxyphenylamino, 4-sulfo-2-methylphenylamino, 3-sulfo-4-methylphenylamino, 2-sulfo-4-methylphenylamino, phenylthio, p-methylphenylthio, o-methylphenylthio, m-methylphenylthio, 2-carboxylphenylthio, pyridin-2-amino, pyridin-3-amino, pyridin-4-amino, 5-bromopyridin-2-amino, 5-bromo-3-nitropyridin-2-amino, 4-methyl-3-nitropyridin-2-amino, 4-methyl-5-nitropyridin-2-amino, 3-nitropyridin-2-amino, 5-nitropyridin-2-amino, 3-methylpyridin-2-amino, 4-methylpyridin-2-amino, 5-methylpyridin-2-amino, 6-methylpyridin-2-amino, 4,6-dimethylpyridin-2-amino, 2-methoxypyridin-5-amino, 5-chloropyridin-2-amino, 2-chloropyridin-3-amino, 2-chloropyridin-5-amino, 3,5-dibromopyridin-2-amino, 3,5-dichloropyridin-2-amino, 4-methyl-3-nitropyridin-2-amino, 4-methyl-5-nitropyridin-2-amino, nicotinamid-6-amino, nicotinamid-2-amino, pyrimidin-2-amino, pyrimidin-4-amino, 5-bromopyrimidin-2-amino, 2,6-dihydroxypyrimidin-4-amino, 4,6-dimethoxypyrimidin-3-amino, 4,6-dimethoxypyrimidin-2-amino, 4-hydroxy-6-methylpyrimidin-2-amino, 3-hydroxypyrimidin-2-amino, 4-methoxy-5-methylpyrimidin-2-amino, 2-methoxypyrimidin-5-amino, 4-chloro-6-methylpyrimidin-2-amino, 6-chloro-2-methylthiopyrimidin-4-amino, 4,6-dichloropyrimidin-2-amino, 4,6-dichloropyrimidin-5-amino, 4-methylpyrimidin-2-amino, 3-nitropyrimidin-2-amino and 5-nitropyrimidin-2-amino.

20. A method of preparing a pharmaceutical composition for selectively inhibiting cyclooxygenase-2, wherein the method comprises
(a) mixing the compound represented by formula I with pharmaceutically acceptable excipients;
(b) diluting the compound represented by formula I with pharmaceutically acceptable excipients; or
(c) encapsulating the compound represented by formula I into a carrier to form a capsule or a vesicle,
wherein formula I is:

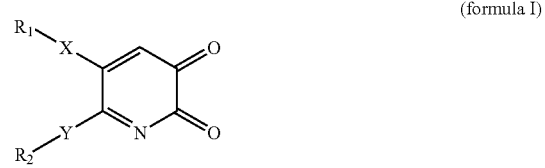

(formula I)

and wherein
$R_1$ and $R_2$ may be the same or different, each independently represents substituted or unsubstituted phenyl, pyridinyl or pyrimidinyl,
X and Y may be the same or different, each independently represents an N or S atom, provided that when X or Y represents S, then the $R_1$ or $R_2$ attached to the S atom is substituted or unsubstituted phenyl.

21. The method of claim 20, wherein when $R_1$ or $R_2$ represents substituted phenyl, substituted pyridinyl or substituted pyrimidinyl, the phenyl, pyridinyl, pyrimidinyl has one to three substituents independently selected from the group consisting of $C_1$-$C_6$ linear or branched alkyl, $C_1$-$C_6$ linear or branched alkoxyl, halogen, amino, di($C_1$-$C_3$ alkyl)amino, carbamyl, sulfamoyl, sulfo, cyano, nitro, carboxyl, hydroxy, hydroxy($C_1$-$C_3$) alkyl, ($C_1$-$C_3$ alkyl)acyl and ($C_1$-$C_3$ alkyl) thio.

22. The method of claim 21, wherein $R_1$—X— and $R_2$—Y— each is independently selected from the group consisting of p-tolylamino, o-tolylamino, m-tolylamino, p-ethylphenylamino, o-ethylphenylamino, m-ethylphenylamino, p-chlorophenylamino, o-chlorophenylamino, m-chlorophenylamino, p-fluorophenylamino, o-fluorophenylamino, m-fluorophenylamino, p-bromophenylamino, o-bromophenylamino, m-bromophenylamino, p-iodophenylamino, o-iodophenylamino, m-iodophenylamino, p-nitrophenylamino, o-nitrophenylamino, m-nitrophenylamino, p-carboxylphenylamino, o-carboxylphenylamino, m-carboxylphenylamino, p-carbamoylphenylamino, o-carbamoylphenylamino, m-carbamoylphenylamino, p-methoxyphenylamino, o-methoxyphenylamino, m-methoxyphenylamino, p-ethoxyphenylamino, o-ethoxyphenylamino, m-ethoxyphenylamino, p-sulfophenylamino, o-sulfophenylamino, m-sulfophenylamino, p-sulfamoylphenylamino, o-sulfamoylphenylamino, m-sulfamoylphenylamino, p-cyanoylphenylamino, o-cyanoylphenylamino, m-cyanoylphenylamino, p-hydroxymethylphenylamino, o-hydroxymethylphenylamino, m-hydroxymethylphenylamino, p-acetylphenylamino, o-acetylphenylamino, m-acetylphenylamino, p-acetaminophenylamino, o-acetaminophenylamino, m-acetaminophenylamino, p-N,N-dimethylaminophenylamino, o-N,N-dimethylaminophenylamino, m-N,N-dimethylaminophenylamino, 2-carboxyl-4-bromophenylamino, 2-carboxyl-6-chlorophenylamino, 2-carboxyl-5-chlorophenylamino, 2-carboxyl-4-chlorophenylamino, 2-carboxyl-3-chlorophenylamino, 3-carboxyl-2-chlorophenylamino, 3-carboxyl-6-chlorophenylamino, 3-carboxyl-4-chlorophenylamino, 4-carboxyl-3-chlorophenylamino, 2-cyano-5-chlorophenylamino, 2-hydroxymethyl-4-chlorophenylamino, 4-carboxyl-5-methoxy-2-chlorophenylamino, 2-sulfo-4-methyl-5-chlorophenylamino, 2-methyl-4-nitro-5-chlorophenylamino, 2-carboxyl-4,6-dichlorophenylamino, 2-carboxyl-4,6-diiodophenylamino, 4-carboxyl-2,6-diiodophenylamino, 2-carboxyl-4,6-dimethoxyphenylamino, 2-cyano-4,6-dimethoxyphenylamino, 4-carbamoyl-2,6-dinitrophenylamino, 2-carboxyl-5-fluorophenylamino, 2-carboxyl-4-fluorophenylamino, 2-carboxyl-3-fluorophenylamino, 2-cyano-3-fluorophenylamino, 2-carboxyl-4-iodophenylamino, 2-carboxyl-6-methoxyphenylamino, 3-carboxyl-6-methoxyphenylamino, 4-carboxyl-6-methoxyphenylamino, 2-carboxyl-4-methylphenylamino, 2-carboxyl-3-methylphenylamino, 3-carboxyl-2-methylphenylamino, 4-carboxyl-2-methylphenylamino, 5-carboxyl-2-methylphenylamino, 2-cyano-5-methylphenylamino, 2-hydroxymethyl-6-methylphenylamino, 2-hydroxymethyl-4-methylphenylamino, 2-methyl-3-hydroxymethylphenylamino, 2-methyl-5-hydroxymethylphenylamino, 2-cyano-4-nitrophenylamino, 4-cyano-2-nitrophenylamino, 2-methyl-4-nitrophenylamino, 2-hydroxy-3-carboxylphenylamino, 3-hydroxy-4-carboxylphenylamino, 3-carboxyl-4-hydroxyphenylamino, 4-sulfo-2-methylphenylamino, 3-sulfo-4-methylphenylamino, 2-sulfo-4-methylphenylamino, phenylthio, p-methylphenylthio, o-methylphenylthio, m-methylphenylthio, 2-carboxylphenylthio, pyridin-2-amino, pyridin-3-amino, pyridin-4-amino, 5-bromopyridin-2-amino, 5-bromo-3-nitropyridin-2-amino, 4-methyl-3-nitropyridin-2-amino, 4-methyl-5-nitropyridin-2-amino, 3-nitropyridin-2-amino, 5-nitropyridin-2-amino, 3-methylpyridin-2-amino, 4-methylpyridin-2-amino, 5-methylpyridin-2-amino, 6-methylpyridin-2-amino, 4,6-dimethylpyridin-2-amino, 2-methoxypyridin-5-amino, 5-chloropyridin-2-amino, 2-chloropyridin-3-amino, 2-chloropyridin-5-amino, 3,5-dibromopyridin-2-amino, 3,5-dichloropyridin-2-amino, 4-methyl-3-nitropyridin-2-amino, 4-methyl-5-nitropyridin-2-amino, nicotinamid-6-amino, nicotinamid-2-amino, pyrimidin-2-amino, pyrimidin-4-amino, 5-bromopyrimidin-2-amino, 2,6-dihydroxypyrimidin-4-amino, 4,6-dimethoxypyrimidin-3-amino, 4,6-dimethoxypyrimidin-2-amino, 4-hydroxy-6-methylpyrimidin-2-amino, 3-hydroxypyrimidin-2-amino, 4-methoxy-5-methylpyrimidin-2-amino, 2-methoxypyrimidin-5-amino, 4-chloro-6-methylpyrimidin-2-amino, 6-chloro-2-methylthiopyrimidin-4-amino, 4,6-dichloropyrimidin-2-amino, 4,6-dichloropyrimidin-5-amino, 4-methylpyrimidin-2-amino, 3-nitropyrimidin-2-amino and 5-nitropyrimidin-2-amino.

23. A method of selectively inhibiting cyclooxygenase-2 for the treatment of inflammation, wherein comprising administrating the compound represented by formula I to a mammal,

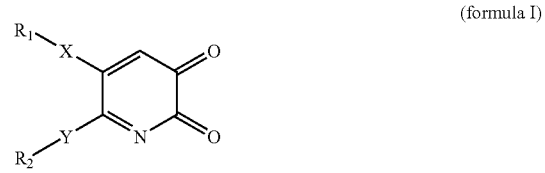

(formula I)

wherein
$R_1$ and $R_2$ may be the same or different, each independently represents substituted or unsubstituted phenyl, pyridinyl or pyrimidinyl,
X and Y may be the same or different, each independently represents an N or S atom, provided that when X or Y represents S, then the $R_1$ or $R_2$ attached to the S atom is substituted or unsubstituted phenyl.

24. The method of claim 23, wherein when $R_1$ or $R_2$ represents substituted phenyl, substituted pyridinyl or substituted pyrimidinyl, the phenyl, pyridinyl, pyrimidinyl has one to three substituents independently selected from the group consisting of $C_1$-$C_6$ linear or branched alkyl, $C_1$-$C_6$ linear or branched alkoxyl, halogen, amino, di($C_1$-$C_3$ alkyl)amino, carbamyl, sulfamoyl, sulfo, cyano, nitro, carboxyl, hydroxy, hydroxy($C_1$-$C_3$) alkyl, ($C_1$-$C_3$ alkyl)acyl and ($C_1$-$C_3$ alkyl)thio.

25. The method of claim 24, wherein $R_1$—X— and $R_2$—Y— each is independently selected from the group consisting of p-tolylamino, o-tolylamino, m-tolylamino, p-ethylphenylamino, o-ethylphenylamino, m-ethylphenylamino, p-chlorophenylamino, o-chlorophenylamino, m-chlorophenylamino, p-fluorophenylamino, o-fluorophenylamino, m-fluorophenylamino, p-bromophenylamino, o-bromophenylamino, m-bromophenylamino, p-iodophenylamino, o-iodophenylamino, m-iodophenylamino, p-nitrophenylamino, o-nitrophenylamino, m-nitrophenylamino, p-carboxylphenylamino, o-carboxylphenylamino, m-carboxylphenylamino, p-carbamoylphenylamino, o-carbamoylphenylamino, m-carbamoylphenylamino, p-methoxyphenylamino, o-methoxyphenylamino, m-methoxyphenylamino, p-ethoxyphenylamino, o-ethoxyphenylamino, m-ethoxyphenylamino, p-sulfophenylamino, o-sulfophenylamino, m-sulfophenylamino, p-sulfamoylphenylamino, o-sulfamoylphenylamino, m-sulfamoylphenylamino, p-cyanoylphenylamino, o-cyanoylphenylamino, m-cyanoylphenylamino, p-hydroxymethylphenylamino, o-hydroxymethylphenylamino, m-hydroxymethylphenylamino, p-acetylphenylamino, o-acetylphenylamino, m-acetylphenylamino, p-acetaminophenylamino, o-acetaminophenylamino, m-acetaminophenylamino, p-N,N-dimethylaminophenylamino, o-N,N-dimethylaminophenylamino, m-N,N-dimethylaminophenylamino, 2-carboxyl-4-bromophenylamino, 2-carboxyl-6-chlorophenylamino, 2-carboxyl-5-chlorophenylamino, 2-carboxyl-4-chlorophenylamino, 2-carboxyl-3-chlorophenylamino, 3-carboxyl-2-chlorophenylamino, 3-carboxyl-6-chlorophenylamino, 3-carboxyl-4-chlorophenylamino, 4-carboxyl-3-chlorophenylamino, 2-cyano-5-chlorophenylamino, 2-hydroxymethyl-4-chlorophenylamino, 4-carboxyl-5-methoxy-2-chlorophenylamino, 2-sulfo-4-methyl-5-chlorophenylamino, 2-methyl-4-nitro-5-chlorophenylamino, 2-carboxyl-4,6-dichlorophenylamino, 2-carboxyl-4,6-diiodophenylamino, 4-carboxyl-2,6-diiodophenylamino, 2-carboxyl-4,6-dimethoxyphenylamino, 2-cyano-4,6-dimethoxyphenylamino, 4-carbamoyl-2,6-dinitrophenylamino, 2-carboxyl-5-fluorophenylamino, 2-carboxyl-4-fluorophenylamino, 2-carboxyl-3-fluorophenylamino, 2-cyano-3-fluorophenylamino, 2-carboxyl-4-iodophenylamino, 2-carboxyl-6-methoxyphenylamino, 3-carboxyl-6-methoxyphenylamino, 4-carboxyl-6-methoxyphenylamino, 2-carboxyl-4-methylphenylamino, 2-carboxyl-3-methylphenylamino, 3-carboxyl-2-methylphenylamino, 4-carboxyl-2-methylphenylamino, 5-carboxyl-2-methylphenylamino, 2-cyano-5-methylphenylamino, 2-hydroxymethyl-6-methylphenylamino, 2-hydroxymethyl-4-methylphenylamino, 2-methyl-3-hydroxymethylphenylamino, 2-methyl-5-hydroxymethylphenylamino, 2-cyano-4-nitrophenylamino, 4-cyano-2-nitrophenylamino, 2-methyl-4-nitrophenylamino, 2-hydroxy-3-carboxylphenylamino, 3-hydroxy-4-carboxylphenylamino, 3-carboxyl-4-hydroxyphenylamino, 4-sulfo-2-methylphenylamino, 3-sulfo-4-methylphenylamino, 2-sulfo-4-methylphenylamino, phenylthio, p-methylphenylthio, o-methylphenylthio, m-methylphenylthio, 2-carboxylphenylthio, pyridin-2-amino, pyridin-3-amino, pyridin-4-amino, 5-bromopyridin-2-amino, 5-bromo-3-nitropyridin-2-amino, 4-methyl-3-nitropyridin-2-amino, 4-methyl-5-nitropyridin-2-amino, 3-nitropyridin-2-amino, 5-nitropyridin-2-amino, 3-methylpyridin-2-amino, 4-methylpyridin-2-amino, 5-methylpyridin-2-amino, 6-methylpyridin-2-amino, 4,6-dimethylpyridin-2-amino, 2-methoxypyridin-5-amino, 5-chloropyridin-2-amino, 2-chloropyridin-3-amino, 2-chloropyridin-5-amino, 3,5-dibromopyridin-2-amino, 3,5-dichloropyridin-2-amino, 4-methyl-3-nitropyridin-2-amino, 4-methyl-5-nitropyridin-2-amino, nicotinamid-6-amino, nicotinamid-2-amino, pyrimidin-2-amino, pyrimidin-4-amino, 5-bromopyrimidin-2-amino, 2,6-dihydroxypyrimidin-4-amino, 4,6-dimethoxypyrimidin-3-amino, 4,6-dimethoxypyrimidin-2-amino, 4-hydroxy-6-methylpyrimidin-2-amino, 3-hydroxypyrimidin-2-amino, 4-methoxy-5-methylpyrimidin-2-amino, 2-methoxypyrimidin-5-amino, 4-chloro-6-methylpyrimidin-2-amino, 6-chloro-2-methylthiopyrimidin-4-amino, 4,6-dichloropyrimidin-2-amino, 4,6-dichloropyrimidin-5-amino, 4-methylpyrimidin-2-amino, 3-nitropyrimidin-2-amino and 5-nitropyrimidin-2-amino.

26. The method of claim 20, wherein the method comprises diluting the compound represented by formula I with pharmaceutically acceptable excipients.

27. The method of claim 26, wherein the pharmaceutical excipients are provided in solid, semisolid, or liquid form as a media for the excipient, the carrier or the compound.

28. The method of claim 27, wherein the pharmaceutical excipients are provided in solid form.

29. The method of claim 28, wherein the pharmaceutical excipients are selected from the group consisting of sugars, celluloses, calcium silicate, poly-vinylpyrrolidone, magnesium stearate, sodium stearate, and glycerol minostearate.

30. The method of claim 27, wherein the pharmaceutical excipients are provided in semisolid or liquid form.

31. The method of claim 30, wherein the pharmaceutical excipients are selected from the group consisting of water, glucose solution, saline, syrup, ethanol, glycerol, propylene glycol, and oil.

* * * * *